United States Patent [19]

Kleiner

[11] 4,056,571

[45] Nov. 1, 1977

[54] PROCESS FOR THE PREPARATION OF TERTIARY PHOSPHINE OXIDES

[75] Inventor: Hans-Jerg Kleiner, Bad Soden, Taunus, Germany

[73] Assignee: Hoechst Aktiengesellschaft, Frankfurt am Main, Germany

[21] Appl. No.: 698,002

[22] Filed: June 21, 1976

Related U.S. Application Data

[60] Continuation of Ser. No. 407,580, Oct. 18, 1973, abandoned, which is a division of Ser. No. 171,305, Aug. 12, 1971, Pat. No. 3,790,638.

[30] Foreign Application Priority Data

Aug. 13, 1970 Germany .............................. 2040208

[51] Int. Cl.$^2$ ........................... C07F 9/28; C07F 9/30; C07F 9/50
[52] U.S. Cl. .............................. 260/583 E; 204/158 R

[58] Field of Search ..................................... 260/583 E

[56] References Cited

U.S. PATENT DOCUMENTS

| 3,442,948 | 5/1969 | Wiley | ........................... 260/583 E X |
| 3,784,638 | 1/1974 | Lambert | ...................... 260/583 E X |

FOREIGN PATENT DOCUMENTS

| 278,688 | 8/1970 | U.S.S.R. | ........................... 260/583 E |

*Primary Examiner*—Paul F. Shaver
*Attorney, Agent, or Firm*—Curtis, Morris & Safford

[57] ABSTRACT

Tertiary phosphine oxides are obtained by adding olefins having a terminal hydroxy or amino group or functional derivatives thereof to secondary phosphine oxides. The adducts are useful as intermediates in the preparation of flame-retardant agents, anti-corrosive agents, pesticides, pharmaceuticals and detergents.

6 Claims, No Drawings

PROCESS FOR THE PREPARATION OF TERTIARY PHOSPHINE OXIDES

This application is a continuation of application Ser. No. 407,580, filed Oct. 18, 1973, which is now abandoned, which, in turn, is a divisional application of Ser. No. 171,305, filed Aug. 12, 1971, now U.S. Pat. No. 3,790,638, dated Feb. 5, 1974.

Aliphatic tertiary phosphine oxides which carry on a carbon radical an optionally substituted hydroxy or amino group, have hitherto not been prepared or only with difficulty. A. B. Bruker et. al. have succeeded in obtaining the 2-dimethyl-phosphinyl ethanol by several steps on the basis of hydroxy ethyl phospine:

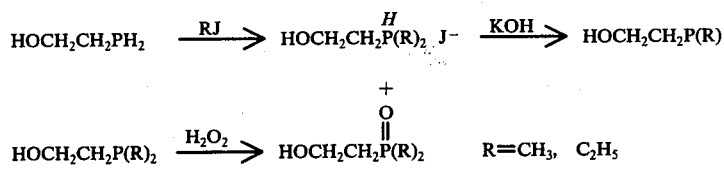

(Z.obsc. Chim. 36 (1966), 484). This process is in no way interesting from a technical point of view.

It has now been found that tertiary phosphine oxides of the formula

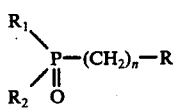   I in which $R_1$ and $R_2$ are alkyl of 1 to 12 carbon atoms or cycloalkyl of 4 to 8 carbon atoms, $n$ is an integer of 2 to 4 and R is a group of the formulae

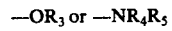

in which $R_3$ is lower alkyl, lower alkanoyl or carbamoyl, or, if $n$ is 3 or 4, hydrogen; $R_4$ is hydrogen, lower alkyl, lower alkanoyl or lower carboalkoxy and $R_5$ is hydrogen or lower alkyl, or —$NR_4R_5$ is a monocyclic 5 to 7 membered saturated or unsaturated heterocyclic residue, may be obtained with a high purity and good yields, if dialkyl phosphine oxides of the formula

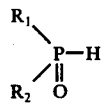   II wherein R and $R^1$ are as defined above, are reacted in the presence of catalytic amounts of free radical-forming agents and/or during exposure to ultraviolet light at a temperature between about 50° and about 250° C with an olefin of the formula

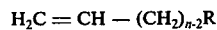   III wherein R and $n$ have the above meanings.

Unless stated otherwise, the above-mentioned lower alkyl groups contain 1 to 4 carbon atoms, they may, thus, represent the methyl, ethyl, propyl or the butyl radical. Lower alkanoyl groups are acyl radicals deriving from low-molecular-weight carboxylic acids, especially those having 1 to 5 carbon atoms, preferably the formyl and the acetyl radical. In analogy to this, lower carboalkoxy stands for a carboxylic acid ester group having from 1 to 4 carbon atoms in the alkanol moiety.

By a heterocyclic 4- to 7-membered radical, there is to be understood above all lactam groups, but also corresponding saturatated and unsaturated nitrogen heterocycles such as pyrrolidine, piperidine, morpholine or 1-imidazolyl radicals.

The dialkyl phosphine oxides used as starting materials according to the invention may be prepared according to the processes described in German Offenlegungschrift Nos. 1,806,705, 1,806,706 and 1,806,707 and the process described in Belgian Pat. No. 737,594. The reaction according to the process of the invention proceeds particularly easily, if the dialkyl phosphine oxides are used in the very pure form as they are obtained according to the above process.

As starting products according to the invention, the different dialkyl phosphine oxides may be employed, the alkyl groups of which contain 1 to 12 preferably 1 to 6, especially 1 to 4 carbon atoms. The alkyl groups may be straight-chained, branched or cyclic, they may be identical or different from one another. There are preferably used alkyl groups having 1 to 4 carbon atoms, that means the methyl, ethyl, propyl or butyl radical. Accordingly there may be used for example: dimethyl phosphine oxide, diethyl phosphine oxide, di-n-butyl-phosphine oxide, dicyclohexyl phosphine oxide, di-n-octyl-phosphine oxide or di-n-dodecyl-phosphine oxide.

There are preferably used olefins of the formula III, in which $n$ is 2 or 3 and R represents a group of the formulae

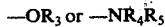

wherein $R_3$ stands for lower alkyl, lower alkanoyl or carbamoyl, and, if $n$ is 3, for hydrogen, $R_4$ represents hydrogen or lower alkyl, and $R^7$ stands for hydrogen, lower alkyl, lower alkanoyl, lower carboalkoxy or the group of the formula

stands for piperidyl, morpholyl, 1-imidazolyl or the group of the formula

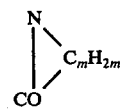

in which $m$ is an integer of from 2 to 5.

The process according to the invention furthermore implies that olefins of the formula III are used, in which $R_3$ is lower alkyl, $n$ is 2 or 3 and R represents lower alkyl, acetyl, carbamoyl or, if $n$ is 3, hydrogen; $R_4$ is hydrogen, methyl or ethyl, $R_5$ is hydrogen or lower carboalkoxy and —$NR_4R_5$ is 1-caprolactamyl or 1-imidazolyl.

Olefins employable for the reaction are for example: allyl alcohols, allyl amine, allyl urethane, vinyl acetate, N-vinylmethylformamide, N-vinyl methyl acetamide, N-vinyl-methyl-carbamic acid methyl ester, N-vinyl-azetidinone-(2), N-vinyl-caprolactam, furthermore vinyl methyl-, vinyl ethyl- or vinyl butyl ether, N-vinyl pyrrolidone, N-vinyl piperidine, N-vinyl morpholine or N-1-vinyl imidazoline.

The used olefins are expediently reacted in a form as pure as possible.

The reaction is carried out at a temperature between about 50° and 250° C, preferably between about 80° and 180° C. Since the reaction is exothermic, heating is generally not required, after the reaction has started. It is advantageous to carry out the reaction under protection of inert gases. As inert gases there are considered especially argon and nitrogen, but also carbon dioxide or a hydrocarbon gas.

The free radical-forming agents are employed in catalytic amounts up to about 5 mol%, preferably about 0.1 to 1 mol%, calculated on the amount of tertiary phosphine oxide theoretically obtainable in the reaction. They are expediently dissolved in the reaction component which is slowly added in the course of the reaction.

As radical-forming agents there are considered for example: The di-tert.butyl peroxide, tert.-butyl-peroxy-benzoate, 2,5-dimethyl-hexane-bis-2,5-(peroxybenzoate), tert.-butyl-hydroperoxide, dicumyl peroxide, azobisiso-butanol diacetate, azobisisobutyronitrile, tert.-butylperoxyethane-nitrile-(2), tert.-butyl-peroxyethane-sulfonic acid-n-butyl ester, dibenzoyl peroxide.

The radical-forming agents are selected with regard to the temperature chosen for the reaction. Within this temperature range the radical-forming agents must have a sufficiently high half-life period. The di-tert.-butyl-peroxide and azobisisobutyronitrile are preferably employed as free radical-forming agents.

The dialkyl phosphine oxide and olefin are preferably used in a molar ratio of about 1:1. However, it is possible to use one of the reaction components in excess, for example up to the fourfold molar amount.

The reaction may also be effected in the presence of inert solvents, for example alcohols, esters and hydrocarbons. However, the reaction is preferably carried out without solvents.

The reaction according to the invention is expediently performed by adding to the dialkyl phosphine oxide the olefin, mixed with catalytic amounts of a free radical-forming agent. Olefins of a low boiling point are preferably added in the way that the supply tube leads under the surface of the dialkyl phosphine oxide. If a free radical-forming agent only dissolves in the secondary phosphine oxide, a part of the whole dialkyl phosphine oxide in which this radical-forming agent is dissolved, may be added separately, besides the olefin added during the reaction.

It is also possible to introduce a tertiary phosphine oxide prepared in a first mixture, as a dissolution-promoting agent, into the reaction vessel and to add simultaneously the reaction components.

This method allows the process to run continuously. In the same rate as olefin and secondary phosphine oxide are introduced into the reaction space, the reaction mixture is removed. In a second reaction vessel this mixture may be kept at a definite temperature until the reaction is completed; it represents the crude tertiary phosphine oxide.

The tertiary phosphine oxides obtained according to the present process may be purified by distillation or recrystallization. They are generally obtained in very pure form. They may be employed as flame-protecting agents, especially the groups having hydroxy groups in the preparation of polyurethanes by adding an effective amount of said compounds, as insecticides or fungicides and as corrosion inhibitors. Since the low-molecular-weight phosphine oxides are water-soluble and since the high-molecular-weight compounds exhibit surface-active properties (U.S. Pat. Nos. 3,304,263, 3,312,627, 3,325,546 and 3,332,875), the new compounds may also yield, with their reactive groups, other compounds having these properties.

Because it is known that secondary alkyl phosphine oxides have the tendency — increasing in the same measure as the number of hydrocarbon atoms in the alkyl radicals are decreasing — to be split up to form secondary phosphines and phosphine acids (Am. Soc. 77/1955, p. 3412), it has been surprising that the above reaction may be performed in the presence of radical-forming agents, especially peroxides and, above all, that it leads to good yields even at elevated temperatures from about 130° to 200° or 250° C which, due to their higher reaction speed, are interesting for technical or continuous preparation processes.

The following Examples illustrate the invention.

EXAMPLE 1

Under a nitrogen atmosphere 610 g of allyl alcohol, mixed with 13 g of azobisisobutyronitrile, were introduced dropwise during 3 hours, into 820 g of dimethyl phosphine oxide at 95°–110° C, while stirring rapidly. Then the whole was distilled. 1233 g of 3-dimethylphosphinyl propanol were obtained, boiling point: 157° C/0.3 torr, which corresponds to a yield of 86.5% of the theory.

$(CH_3)_2P(O)CH_2CH_2CH_2OH$: Calc: 44.1% C; 9.56% H; 22.75% P. Found: 44.2% C; 9.4% H; 22.5% P.

EXAMPLE 2

Under a nitrogen atmosphere, 576 g of allyl amine, mixed with 13 g of di-tert.-butylperoxide, were introduced dropwise at 140°–150° C in the course of 3 hours into 788 g of dimethyl phosphine oxide, while stirring vigorously, the supply tube of the dropping funnel leading under the surface of the dimethyl phosphine oxide. Then the whole was distilled. 1248 g of 3-dimethyl phosphinyl propyl amine were obtained, boiling point 126° C/0.3 torr, solidification point: 39.5° C, which corresponds to a yield of 91.5% of the theory $(CH_3)_2P(O)CH_2CH_2CH_2NH_2$: Calc: 55.3% C; 9.23% H; 6.45% N; 14.3% P. Found: 55.0% C; 9.1% H; 6.2% N; 14.1% P.

EXAMPLE 3

Under a nitrogen atmosphere, 344 g of vinyl acetate mixed with 1 g of azobisisobutyronitrile were introduced dropwise at 140°–150° C in the course of 1 hour into 312 g of dimethyl phosphine oxide, while stirring vigorously. Stirring was continued for 20 minutes at this temperature. The whole was distilled. 565 g of 2-dimethylphosphinyl ethyl acetate were obtained, boiling point: 130°–140° C/0.5 Torr, which corresponds to a yield of 86% of the theory.

EXAMPLE 4

Under a nitrogen atmosphere, 191 g of N-vinyl-methyl acetamide, mixed with 1 g of azobisisobutyronitrile were introduced dropwise at 90°-Ψ° C in the course of 2 hours into 150 g of dimethyl phosphine oxide, while stirring vigorously. When the reaction was completed, the reaction mixture was distilled. 281 g of N-2-dimethyl-phosphinyl ethyl-methyl acetamide were obtained, boiling point: 175°-180° C/0.4 Torr, melting point 80°-90° C, which corresponds to a yield of 83.5% of the theory.

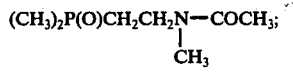

Calc: 47.5% C; 9.05% H; 7.92% N; 17.5% P. Found: 47.0% C; 9.3% H; 8.0% N; 17.4% P.

EXAMPLE 5

Under a nitrogen atmosphere, 170 g of N-vinylmethylformamide, mixed with 1.5 g of di-tert.-butylperoxide were introduced dropwise at 145°-155° C into 156 g of dimethyl phosphine oxide. 295 g of N-2-dimethyl phosphinyl-ethyl methyl formamide were obtained, boiling point: 182° C/0.8 Torr, which corresponds to a yield of 90.5% of the theory.

Calc: 44.2% C; 8.6% H; 8.6% N; 19.0% P. Found: 44.1% C; 8.4% H; 8.2% N; 20.0% P.

EXAMPLE 6

Under a nitrogen atmosphere, 239 g of N-vinyl caprolactame mixed with 2 g of azobisisobutyronitrile, were introduced dropwise into 134 g of dimethyl phosphine oxide at 90°-100° C in the course of 1.5 hours, while stirring vigorously. Stirring was continued for 30 minutes at this temperature. Then the whole was distilled. 270 g of N-2-dimethyl phosphinylethyl caprolactame, boiling point: 180°-205° C/0.3 Torr, melting point: 110°-115° C, which corresponds to a yield of 72.5% of the theory.

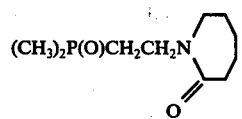

Calc: 55.3% C; 9.23% H; 6.45% N; 14.3% P. Found: 55.0% C; 9.1% H; 6.2% N; 14.1% P.

EXAMPLE 7

Under a nitrogen atmosphere, 178.5 g of N-vinyl-methyl carbamic acid ethyl ester, mixed with 3 g of azobisisobutyronitrile were introduced dropwise into 108 g of dimethyl phosphine oxide at 90°-110° C in the course of 1.5 hours, while stirring well. When the reaction was completed, the whole was distilled. 236 g of N-2-dimethyl phosphinyl ethyl-N-methyl-carbamic acid ethyl ester were obtained, boiling point: 150° C/0.4 Torr, which corresponds to a yield of 83% of the theory.

Calc: 46.3% C; 8.7% H; 6.76% N; 14.95% P. Found: 46.4% C; 8.7% H; 6.4% N; 15.0% P.

EXAMPLE 8

Under a nitrogen atmosphere 78 g of a vinyl acetate and 0.5 g of azobisisobutyronitrile were introduced dropwise, as a mixture, at 100° C to 95 g of diethyl phosphine oxide, while stirring vigorously. The reaction was completed after 1 hour. Then the whole was distilled. 155 g of 2-diethyl phosphinyl ethyl acetate were obtained, boiling point: 126° C/0.5 Torr, which corresponds to a yield of 89% of the theory.

$(C_2H_5)_2P(O)CH_2CH_2OCOCH_3$: Calc: 50.0% C; 8.85% H; 16.1% P. Found: 49.7% C; 8.7% H; 15.9% P.

EXAMPLE 9

Under a nitrogen atmosphere, a mixture of 77 g of vinyl isobutyl ether and 1 g of di-tert.-butylperoxide were introduced dropwise into 60 g of dimethyl phosphine oxide while stirring vigorously. The reaction was completed after 1.5 hours. Then the whole was distilled. 115 g of 2-(dimethyl phosphinylethyl) isobutyl ether were obtained, boiling point: 114° C/0.4 Torr, melting point: 38°-40° C, which corresponds to a yield of 84% of the theory.

$(CH_3)_2P(O)CH_2CH_2OCH_2CH(CH_3)_2$: Calc: 53.8% C; 10.68% H; 18.0% P. Found: 53.9% C; 10.5% H; 17.8% P.

EXAMPLE 10

250 g of dimethyl phosphine oxide were mixed with 100 g of allyl alcohol and heated with reflux to 150° C under a nitrogen atmosphere. The mixture was exposed to ultraviolet light with the aid of an immersion lamp. In the course of 6 hours, further 82 g of allyl alcohol were slowly introduced dropwise, the reflux temperature increasing to 158° C. Then the whole was distilled. At first, non reacted starting materials were obtained which could be employed again and then 220 g of 3-dimethyl phosphinyl propanol were obtained, boiling point: 157° C/0.3 Torr. The residue of distillation amounted to 20 g, which corresponds to a yield of about 50%.

$(CH_3)_2P(O)CH_2CH_2CH_2OH$: Calc: 44.1% C; 9.56% H; 22.75% P. Found: 44.5% C; 9.2% H; 24.0% P.

EXAMPLE 11

Under a nitrogen atmosphere, 50.5 g of carbamic acid allyl ester, mixed with 0.25 g of azobisisobutyronitrile were added dropwise, while stirring vigorously, at 95°-105° C to 39 g of dimethylphosphine oxide, at such a rate that the temperature remained constant. After 3 hours the reaction was completed. The reaction product was dissolved in 130 ml of acetonitrile and cooled. 75 g of crystallized carbamic acid-3-dimethyl-phosphinyl propyl ester were obtained, melting point: 122°-123° C, which corresponds to a yield of 84% of the theory.

$(CH_3)_2P(O)CH_2CH_2CH_2OCONH_2$: Calc: 40.3% C; 7.83% H; 7.83% N; 17.3% P. Found: 40.1% C; 7.8% H; 7.6% N; 17.5% P.

EXAMPLE 12

Under a nitrogen atmosphere, 69 g of allyl diethyl amine, mixed with 0.4 g of di-tert.-butyl peroxide, were added dropwise at 150° C to 47 g of dimethyl phosphine oxide, while stirring vigorously. After 1 hour and 45 minutes, the reaction was completed. Then the product was distilled. 109 g of 3-dimethyl phosphinyl propyl diethyl amine were obtained, which corresponds to a yield of 94.5% of the theory.

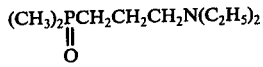

Calc: 56.5% C; 11.5% H; 7.34% N; 16.24% P. Found: 56.4% C; 11.55% H; 7.31% N; 16.0% P.

EXAMPLE 13

80 g of dimethyl phosphine oxide were heated to 150° C under a nitrogen atmosphere and a mixture of 96.5 g of N-vinyl-imidazole and 1 g of di-tert.-butyl peroxide was added dropwise in the course of 1 hour while stirring vigorously. When the reaction was completed, the reaction product solidified when cooling. The crude product was recrystallized from dioxan. 140 g of N-1-dimethyl phosphinylethyl imidazol were obtained, melting point: 111°–115° C, which corresponds to a yield of 79.5% of the theory.

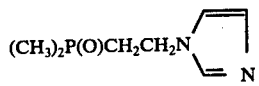

Calc: 48.75% C; 7.55% H; 16.3% N; 18.0% P. Found: 48.7% C; 7.43% H; 16.0% N; 17.5% P.

EXAMPLE 14

3-Hydroxypropyl-dimethyl phosphine oxide is reacted with an excess of thionyl chloride by heating with reflux until no longer sulfur dioxide is set free. By distillation the so-obtained 3-chloropropyl-dimethyl phosphine oxide is isolated. This compound is useful for rendering the known tranquillizer 7-chloro-1,3-dihydro-5-phenyl-2H-1,4-benzodiazepine-2-one water-soluble: 4.4 g of (0.1 mole) of sodium hydride (about 55% strength in parafin oil) were added to 24 g (0.089 mole) of 7-chloro-1,3-dihydro-5-phenyl-2H-1,4-benzodiazepine-2-one on 400 ml of absolute toluene and the whole was boiled for 15 hours under reflux. After addition of 15 g (0.097 mole) of 3-chloropropyl-dimethyl-phosphine-oxide, the whole was stirred for further 8 hours under reflux, while stirring, and the sodium chloride that had precipitated was then filtered off. The solvent was removed under reduced pressure and the residue was stirred with 250 ml of 50° C hot water. The filtered aqueous solution was then treated with active charcoal. The benzodiazepine of the invention was isolated by exhaustive extraction with ethyl acetate. After drying over sodium sulfate, the solvent was removed by distillation under reduced pressure. Upon standing, the 7-chloro-1,3-dihydro-1-dimethyl-oxophosphinyl-n-propyl-5-phenyl-2H-1,4-benzodiazepine-2-one (16 g = 47% of the theory) crystallized. For purification, the compound which was found to be soluble in water was recrystallized from a mixture of benzene and cyclohexane (1:1). The structure of the compound, which was found to melt at 154° C, was proved by the data obtained by IR-, NMR- and MS-spectroscopy.

$C_{20}H_{22}ClN_2O_2P$ (388.5): Calc: C 61.7%; H 5.6%; P 7.98%; Found: C 61.5%; H 5.6%; P 7.8%.

I claim:

1. A compound of the formula

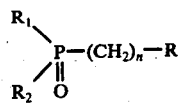

in which $R_1$ and $R_2$ are alkyl of 1 to 12 carbon atoms, $n$ is 3, and R is

in which $R_4$ is hydrogen, and $R_5$ is hydrogen.

2. The compound as defined in claim 1, in which $R_1$ and $R_2$ are methyl.

3. The compound as defined in claim 1, wherein $R_1$ and $R_2$ are ethyl.

4. A compound of the formula

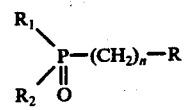

in which $R_1$ and $R_2$ are cycloalkyl of 4 to 8 carbon atoms, $n$ is 3, and R is

in which $R_4$ is hydrogen, and $R_5$ is hydrogen.

5. A process for the preparation of a compound

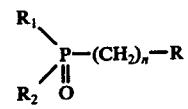

in which $R_1$ and $R_2$ are alkyl of 1 to 12 carbon atoms, $n$ is 3, and R is

in which $R_4$ is hydrogen, and $R_5$ is hydrogen, and which comprises reacting a dialkyl phosphine oxide of the formula

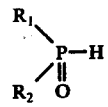

wherein $R_1$ and $R_2$ are as defined above, with an olefin of the formula

wherein R and $n$ have the above meanings, in the presence of a catalytic amount of a free radical-forming agent at a temperature between 80° and about 180° C.

6. A process as defined in claim 5, wherein instead of using a free radical-forming agent, the reaction mixture is exposed to ultraviolet light.

* * * * *

UNITED STATES PATENT AND TRADEMARK OFFICE
CERTIFICATE OF CORRECTION

PATENT NO. : 4,056,571
DATED : November 1, 1977
INVENTOR(S) : Kleiner

It is certified that error appears in the above—identified patent and that said Letters Patent are hereby corrected as shown below:

In the Heading, Item "[30]" line 2, change "2040208" to --20 40 280--.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*